United States Patent [19]

Collins et al.

[11] Patent Number: 4,463,013
[45] Date of Patent: Jul. 31, 1984

[54] OXYGEN SUBSTITUTED AMINO-CYCLOHEXYL-BENZENEACETAMIDES AND -BENZAMIDES AS WATER DIURETIC DRUGS

[75] Inventors: Robert J. Collins; Lester J. Kaplan, both of Kalamazoo; James H. Ludens, Portage; Philip F. Von Voigtlander, Gunplain Township, Allegan County, all of Mich.

[73] Assignee: The Upjohn Company, Kalamazoo, Mich.

[21] Appl. No.: 409,225

[22] Filed: Aug. 18, 1982

Related U.S. Application Data

[63] Continuation-in-part of Ser. No. 366,908, Apr. 9, 1982, abandoned.

[51] Int. Cl.$^3$ ............................................. A61K 31/40
[52] U.S. Cl. .................................... 424/274; 424/244; 424/267; 424/275; 424/278; 424/285; 548/407
[58] Field of Search ............... 424/244, 267, 274, 275, 424/285, 278

[56] References Cited

U.S. PATENT DOCUMENTS

| | | | |
|---|---|---|---|
| 4,145,435 | 3/1979 | Szmuszkovicz | 424/274 |
| 4,212,878 | 7/1980 | Lednicer et al. | 424/274 |
| 4,359,476 | 11/1982 | Kaplan et al. | 424/274 |
| 4,360,531 | 11/1982 | McMillan et al. | 424/274 |

OTHER PUBLICATIONS

*Physicians' Desk Reference*, (PDR), 35th Edition, (1981), published by Litton Industries, Medical Economics Company, p. 217.
Nutt, J. et al., *Clinical Pharmacology and Therapeutics*, 15, (1974), pp. 361–367.
Martin, W. et al., *The Journal of Pharmacology and Experimental Therapeutics*, 197, No. 3, (1976), pp. 517–532.
Greidanus, T. et al., *Life Sciences*, 24, No. 7, (1979), pp. 579–585.
Firemark, H. et al., *Neuroscience*, 4, pp. 1895–1902, (1979).

*Primary Examiner*—Richard A. Schwartz
*Attorney, Agent, or Firm*—John T. Reynolds

[57] ABSTRACT

Conditions of inappropriate hyperhydration in warm blooded animals can be treated with an essentially water only diuretic drug compound selected from the group

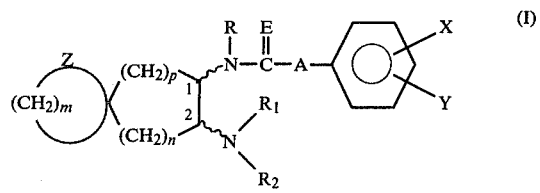

wherein m, n, p, A, E, R, $R_1$, $R_2$, X, Y and Z are as defined in the specification, e.g., trans-3,4-dichloro-N-methyl-N-[7-(1-pyrrolidinyl)-1,4-dioxaspiro[4.5]dec-8-yl]benzeneacetamide, or a pharmaceutically acceptable salt thereof,

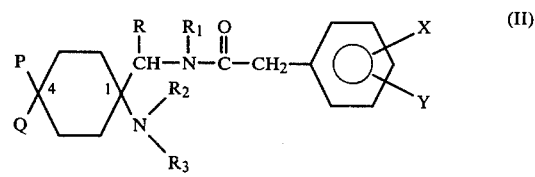

wherein R, $R_1$, $R_2$, $R_3$, P, Q, X and Y are as defined in the specification, e.g., 3,4-dichloro-N-[[8-(1-pyrrolidinyl)-1,4-dioxaspiro[4.5]-dec-8-yl]methyl]benzeneacetamide, or a pharmaceutically acceptable salt thereof, or

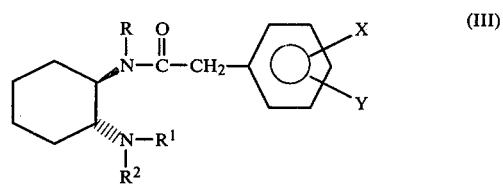

where R, $R^1$, $R^2$, X and Y are as defined in the specification, e.g., trans-(1)-2-(3,4-dichlorophenyl)-N-methyl-N-[2-(1-pyrrolidinyl)cyclohexyl]acetamide, or

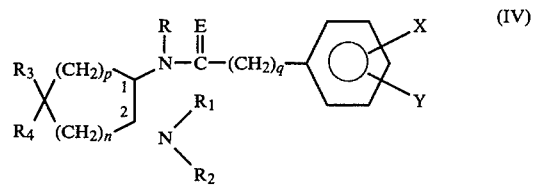

wherein p, n, q, X, Y, R, $R_1$, $R_2$, $R_3$, $R_4$, E, $R_5$, $R_6$ are as defined in the specification, or

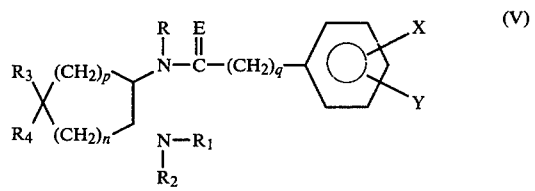

wherein R, $R_1$, $R_2$, $R_3$, $R_4$, X, Y, p, n, q, E, are as defined in the specification,
or a pharmaceutically acceptable salt thereof.

4 Claims, No Drawings

OXYGEN SUBSTITUTED AMINO-CYCLOHEXYL-BENZENEACETAMIDES AND -BENZAMIDES AS WATER DIURETIC DRUGS

CROSS REFERENCE

This is a continuation-in-part of Application Ser. No. 366,908, filed Apr. 9, 1982 now abandoned.

INTRODUCTION

This invention relates to the use of certain N-(2-aminocyclohexyl)benzeneacetamide and -benzamide compounds as water diuresis drugs in treating warm blooded animal patients suffering from inappropriate hyperhydration conditions. More particularly, this invention provides a process or method for treating patients suffering from inappropriate hyperhydration to remove water via the urine without materially upsetting the sodium, potassium, chlorine, bicarbonate and other ion balance in the patient.

BACKGROUND OF THE INVENTION

In a variety of clinical (valuable animal and human treatment) situations, dilution of electrolytes in extracellular fluids (inappropriate hyperhydration) of the body can be a problem in itself or a problem which interferes with the treatment of other associated abnormal or disease conditions of concern to the patient and/or physician. Examples of clinical circumstances that can be associated with inappropriate hyperhydration (dilutional problems) include congestive heart failure, advanced hepatic cirrhosis, nephrotic syndrome, chronic renal failure, trauma associated with surgery, emotional and physical stress, endocrine disorders, syndrome of inappropriate antidiuretic hormone (ADH) secretion and therapy with certain pharmacologic drug agents, such as certain sulfonylureas, certain biguanides like phenformin and metformin, clofibrate, certain tricyclics like carbamazepine, amitriptyline, thiothixene, fluphenazine and thioridazine, certain antineoplastic agents, certain analgesics and certain natriuretic diuretics.

Many diuretic drug compounds are known and lists of various commercially available diuretics can be found in various publications, e.g., the *Physicians' Desk Reference* (PDR), 34th Edition (1980), published by Charles E. Baker, Jr., Copyright 1980 by Litton Industries, Inc., Published by Medical Economics Company, a Litton division at Oradell, N.J. 07649, under DIURETICS on pp. 216-217 thereof. However, at least some of these known listed diuretic agents cause excretion of substantial amounts of important body electrolytes such as sodium, potassium, chloride, bicarbonate and other ions in addition to the water involved, necessitating that care is taken to avoid the urinary elimination of too much of the ions (electrolytes) needed to maintain normal ion balance in the body.

It would be desirable to provide to diuretic drug users and physicians concerned with inappropriate hyperhydration conditions associated with any of the above conditions, a drug means to cause the kidney to form a urine which is more dilute than normal to correct or counterbalance the dilution of extracellular fluids (inappropriate hyperhydration condition) associated with various water situations such as those cited above.

OBJECTS OF THE INVENTION

It is an object of this invention to provide the medical, including the veterinary, profession with some more potent diuretic drug compounds which help alleviate problem dilutions of electrolytes in extracellular fluid (inappropriate hyperhydration) conditions and which drug compounds have little or no effect on normal urinary sodium, potassium and chloride ion excretion rates.

It is another object of this invention to provide a process for treating warm-blooded animal patients, including humans, suffering from dilution of extracellular fluids (inappropriate hyperhydration) to relieve or alleviate the excess body water condition in such patients, without having any substantial effect on the electrolyte balance of the patient's body.

It is also an object of this invention to define and describe how to use certain N-[2-aminocyclohexyl]benzeneacetamide and -benzamide derivative compounds as essentially 'water only' diuretic drugs in valuable animal and human patients to alleviate conditions of abnormal dilution of extracellular fluids (inappropriate hyperhydration) without materially altering the normal electrolyte balance in the patient's body.

Other objects, aspects and purposes of the invention will be apparent from reading the remaining specification and the claims which follow.

SUMMARY OF THE INVENTION

Briefly, we have discovered that certain N-(2-aminocyclohexyl)benzeneacetamide and -benzamide derivative compounds, of structures I to V hereinbelow, increase urinary volume but have little or no effect on urinary sodium, potassium or chloride or other ion excretion. That is, these compounds cause the kidney to make a very dilute urine. These compounds were originally discovered and found to be useful as part of five classes of analgesic compounds. Further studies showed that members of the defined structure I to V compounds were also active as substantially 'water-only' diuretics at reasonable dosage ranges.

DETAILED DESCRIPTION OF THE INVENTION

More particularly, this invention provides a process for treating a warm-blooded animal patient suffering from dilution of the extracellular fluids (inappropriate hyperhydration) which comprises administering to such patient a safe, non-toxic amount of a compound of a formula selected from the group consisting of

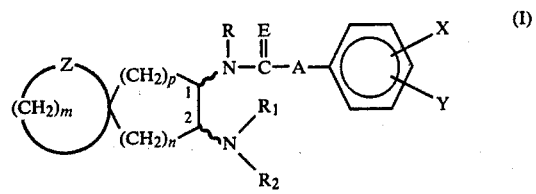

wherein p is a whole number integer 0, 1 or 2 and n is a whole number integer 1, 2 or 3, so that the resulting cycloaliphatic ring containing them has six (6) carbon atoms;

m is 3 or 4;

A is $-(CH_2)_q$ where q is a whole number integer 1 to 4, $-CH(CH_3)-$, or A is a single chemical bond $(-)$ only when R and R₂ are taken together with the nitrogen to which they are bonded to complete a ring amine group set forth below;

X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxyacylamino (—NHC(=O)R₄ where R₄ is hydrogen or $C_1$ to $C_2$-alkyl);

R is hydrogen or $C_1$ to $C_3$-alkyl;

R₁ and R₂, taken separately, are each hydrogen, $C_1$ to $C_3$-alkyl or allyl,

R₁ and R₂, taken together with the nitrogen to which they are bonded, complete a ring selected from the group consisting of azetidinyl, pyrrolidinyl and piperidinyl, pyrrolyl, 3-pyrrolinyl, 3-azabicyclo[3.1.0]hexan-3-yl and 3-azabicyclo[3.2.0]heptan-3-yl;

E is oxygen or sulfur;

Z is selected from the group consisting of oxygen, bivalent sulfur, and sulfinyl;

provided that the diuretically active formula I compound contains an isomer thereof with an S absolute structural configuration at each of the one and two positions of the cyclohexane ring carbons bonded to the nitrogen atoms;

or a pharmacologically acceptable salt thereof; or

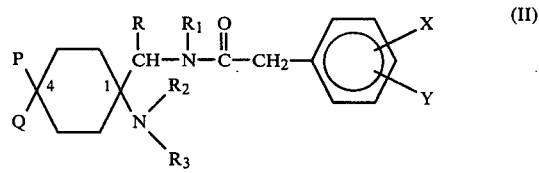

wherein

R is hydrogen or $C_1$ to $C_3$-alkyl;

R₁ is hydrogen or $C_1$ to $C_3$-alkyl;

R₂ and R₃, taken together with the nitrogen to which they are bonded, complete a mono-nitrogen heterocyclic ring having from 3 to 4 ring carbon atoms and no other hetero-atoms in the ring;

Q and P taken together represent an oxo (O) group or a $C_2$ to $C_3$-alkylenedioxy group, that is, a group of the formula

where n is 2 to 3; and, taken separately, when P or Q is hydroxy, then the other of Q or P is hydrogen, $C_1$ to $C_3$-alkyl, or phenylalkyl with alkyl being of 1 to 2 carbon atoms;

each of X and Y is selected from the group consisting of hydrogen, $C_1$ to $C_3$-alkyl, $C_1$ to $C_3$-alkyloxy, a halogen having an atomic number of from 9 to 35, nitro, trifluoromethyl, and azido, providing that when X is halogen, Y is $C_1$ to $C_3$-alkyl, $C_1$ to $C_3$-alkyloxy or halogen and that when X is nitro, trifluoromethyl or azido, Y is hydrogen;

or a pharmaceutically acceptable salt thereof;

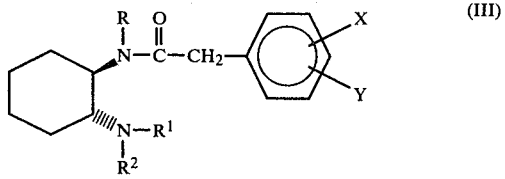

where

R is hydrogen or methyl;

R¹ and R², taken separately, are hydrogen, $C_1$ to $C_3$-alkyl, or when R¹ is hydrogen or $C_1$ to $C_3$-alkyl, R² is allyl;

R¹ and R², taken together with the nitrogen to which they are bonded, complete a ring selected from the group consisting of azetidinyl and pyrrolidinyl;

X and Y are independently selected from the group consisting of hydrogen, a halogen having an atomic number of from 9 to 35, trifluoromethyl, $C_1$ to $C_3$-alkyl, methoxy, azido and phenyl, and at least one of X and Y is a substituent other than hydrogen, and when one of X and Y is azido, phenyl, methoxy or trifluoromethyl, the other of X and Y is hydrogen, and when R is hydrogen, both of X and Y are substituents other than hydrogen, which compounds of Formula III contain the compound having an (S,S) absolute configuration;

or a pharmaceutically acceptable salt thereof; or

A compound of the formula

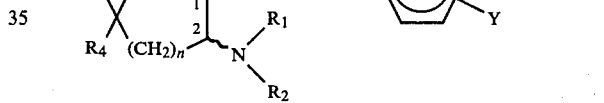

wherein p and n are each full number integers of from 1 to 3, so that the resulting cycloaliphatic ring has five to seven carbon atoms; the wavy line bond (∼) between the nitrogen in the 2-position and the cycloaliphatic ring carbon indicates the bond can be either cis- or trans- with respect to each substituent on the cycloaliphatic ring;

q is 0 or 1;

X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxyacylamino;

R is hydrogen or $C_1$ to $C_3$-alkyl;

R₁ and R₂, taken separately, are hydrogen, $C_1$ to $C_3$-alkyl, allyl, or

R₁ and R₂, taken together with the nitrogen to which they are bonded, complete a ring selected from the group consisting of azetidinyl, pyrrolidinyl, and piperidinyl;

R₃, taken separately, is hydrogen, hydroxy, —OR₅ or OC(=O)R₆;

R₄, taken separately, is hydrogen;

R₃ and R₄, taken together, are selected from the group consisting of —ECH₂CH₂E—;

=E,

=N∼OH and $=N\sim OC(O)CH_3$;

wherein each E is bivalent sulfur or oxygen and $R_3$ and $R_4$ cannot both be hydrogen at the same time;

$R_5$ is $C_1$ to $C_3$-alkyl;

$R_6$ is hydrogen or $C_1$ to $C_2$-alkyl; or an acid addition salt thereof;

provided that when R is methyl, $R_1$ and $R_2$, taken together with the nitrogen to which they are bonded, form a pyrrolidinyl;

X and Y are each chlorine in the 3- and 4-positions of the phenyl ring;

p is 1;

n is 2;

q is 1;

E is oxygen;

R is hydrogen then $R_3$ cannot be acetoxy and a 5-alpha orientation (on the same side of the cycloaliphatic ring as the amide nitrogen);

or a compound of the formula

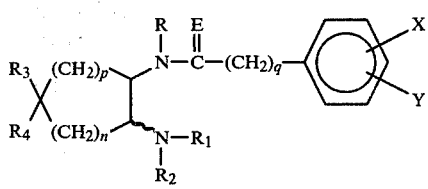 (V)

wherein

R is hydrogen or $C_1$ to $C_3$-alkyl;

$R_1$ and $R_2$, taken separately, are each hydrogen or $C_1$ to $C_3$-alkyl;

$R_1$ and $R_2$, taken together with the nitrogen to which they are bonded, are azetidinyl, pyrrolidinyl or piperidinyl;

$R_3$, taken separately, is hydroxy, $C_1$ to $C_2$-alkyloxy, or $C_1$ to $C_3$-alkanoyloxy;

$R_4$, taken separately, is hydrogen when $R_3$ is hydroxy, $C_1$ to $C_2$-alkyloxy, or $C_1$ to $C_3$-alkanoyloxy;

$R_3$ and $R_4$, taken together, complete a moiety selected from the group, $=G$ (oxo or thioxo), $-G-CH_2CH_2-G-$, $-G-CH_2CH_2CH_2-G-$, $-G-CH_2CH(CH_3)CH_2-G-$, $-G-CH_2C(CH_3)_2CH_2-G-$, wherein both G moieties in the same group are oxygen or bivalent sulfur, $=N\sim OH$, and $=N\sim OC(=O)CH_3$, wherein each G is oxygen or bivalent sulfur;

X and Y are independently selected from the group consisting of hydrogen, a halogen having an atomic number from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino($-NHC(=O)R_6$, wherein $R_6$ is hydrogen or $C_1$ to $C_2$-alkyl;

p and n are whole number integers selected from the group zero, 2, 3, or 4, such that one of p and n is zero and the other of p and n is 2, 3, or 4;

q is zero or 1;

E is oxygen or bivalent sulfur;

provided that when R is $C_1$ to $C_3$-alkyl, $R_1$ and $R_2$, taken together with the nitrogen to which they are bonded, complete a pyrrolidinyl ring;

p is 3 and n is 0;

q is 1;

X and Y are chlorine in the 3 and 4 positions, $R_3$ is not hydroxy, $C_1$ to $C_2$-alkoxy or $C_1$ to $C_3$-alkanoyloxy;

or a pharmaceutically acceptable salt thereof.

Methods known in the art for the determination of absolute configuration of chemical compounds, including the above compounds, are exemplified x-ray crystallography procedures, circular dichroism (CD) procedures, optical rotary dispersion (ORD) procedures, nuclear magnetic resonance (NMR) spectroscopy in a chiral environment, and the like.

Examples of acids suitable for making pharmaceutically acceptable acid addition salts of the above compounds of formulas I, II, III, IV and V above for use according to this invention include such acids as hydrogen chloride, hydrogen bromide, hydrogen iodide, sulfuric acid, orthophosphoric acid, acetic acid, lactic acid, citric acid, succinic acid, benzoic acid, salicyclic acid, pamoic acid, cyclohexanesulfonic acid, methanesulfonic acid, 1- and 2-naphthalene sulfonic acids, p-toluenesulfonic acid, maleic acid, fumaric acid, and the like.

The term "inappropriate hyperhydration" as used herein means that the body contains an abnormal or excess total amount of water including extracellular water and water in cells and tissues relative to the amount of electrolytes in the body compartments. This term is intended to include the treatment of conditions where there is an abnormally high amount of water in the body relative to a given amount of electrolytes in the body, but also conditions wherein there may be less electrolytes than is considered normal for the amount of water present in the mammal body being treated.

Dosage ranges for use of these compounds can vary from about 0.001 to about 25 mg/kg of the patient's body weight depending upon the compound being used and the extent of diuresis of the patient desired. A general daily dosage range of from about 0.1 to about 350 mg in single or divided dosage unit forms given two to four times a day for an adult animal is suggested. A single adult human dose ranging from about 0.1 to about 1000 mg per day can be used depending upon the condition being treated, the age and weight of the patient, the compound being used, and similar factors.

For treating some conditions such as hyponatremia associated with antihypertensive therapy, a physician may desire to prescribe the use of one of these formula I, II, III, IV, and V compounds for use in concommitent administration with other diuretics such as hydrochlorthiazide, trichlormethiazide, furosemide, ethoxzolamide, chlorthaidone, triamterene, spironolactone, and the like, to eliminate excess amounts of some electrolytes in the patient's body. For example, for treating a hyponatremic condition, a physician might want to prescribe the patient taking from 0.1 to 1000 mg/day of one of these Formula I to V compounds, or a salt thereof, concommitent with 10 to 200 mg/day of hydrochlorthiazide.

Also, in accordance with this invention, the Formula I to V compounds can also be used concommitently with the usual dosages of antihypertensive drugs such as reserpine, deserpidine, hydralazine hydrochloride, mecamylamine hydrochloride, guanethedine sulfate, methyldopa, pentaerythritol tetranitrate, minoxidil, propranolol, captopril, or the like.

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification under preferred embodiments, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-amide active ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.1 to about 350 mg of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain water diuretic effects within the aforesaid effective non-toxic range. Preferred dosages for most applications are 0.05 to 2.0 mg per kg of body weight.

The useful pharmaceutical dosage unit forms of these compounds in pharmaceutical formulations are preferably adapted for systemic administration to obtain water diuresis effects comprising an effective, non-toxic amount of a compound according to Formula I, II, III, IV, and V or as its pharmacologically acceptable salt.

Examples of compounds of Formula I above which can be used in this invention include:
(1) trans-3,4-dichloro-N-methyl-N-[8-(1-pyrrolidinyl)-1,4-dioxaspiro[4.5]dec-7-yl]benzeneacetamide,
(2) trans-3,4-dichloro-N-methyl-N-[7-(1-pyrrolidinyl)-1,4-dioxaspiro[4.5]dec-8-yl]benzeneacetamide,
(3) trans-3,4-dichloro-N-methyl-N-[7-(1-pyrrolidinyl)-1,4-dioxaspiro-[4.5]dec-6-yl]benzeneacetamide,
(4) trans-4-bromo-N-methyl-N-[7-(1-pyrrolidinyl)-1,4-dioxaspiro[4.5]-dec-8-yl]benzamide,
(5) (5$\alpha$, 7$\alpha$,8$\beta$)-($\pm$)-3,4-dichloro-N-methyl-N-[7-(1-pyrrolidinyl)-1-oxaspiro[4.5]dec-8-yl]benzeneacetamide and its levo isomer (6),
(6) (5$\alpha$, 7$\alpha$, 8$\beta$)-(−)-3,4-dichloro-N-methyl-N-[7-(1-pyrrolidinyl)-1-oxaspiro[4.5]dec-8-yl]benzeneacetamide, and
(7) (5$\xi$, 6$\alpha$, 7$\beta$)-3,4-dichloro-N-[7-(dimethylamino)-1-oxaspiro[4.5]dec-6-yl]-N-methylbenzeneacetamide, and the like,
or a pharmaceutically acceptable salt thereof.

Examples of compounds of Formula II above which can be used according to this invention include
(1) 2-(3,4-dichlorophenyl)-N-[[8-(1-pyrrolidinyl)-1,4-dioxaspiro[4.5]dec-8-yl]methyl]acetamide, which can also be named 3,4-dichloro-N-[[8-(1-pyrrolidinyl)-1,4-dioxaspiro[4.5]dec-8-yl]methyl]benzeneacetamide.
(2) N-[[1-(N-pyrrolidinyl)-4-oxocyclohex-1-yl]methyl]-2-(3-bromo-4-methoxyphenyl)acetamide, ethylene ketal, and the like,
or a pharmaceutically acceptable salt thereof.

Examples of compounds of Formula III which can be used according to this invention include:
trans-N-[2-(1-pyrrolidinyl)cyclohexyl]-N-methyl-2-(3,4-dichlorophenyl)acetamide,
trans-N-[2-(1-pyrrolidinyl)cyclohexyl]-N-methyl-2-(3,4-dichlorophenyl)propionamide,
trans-N-[2-(3-hydroxy-1-pyrrolidinyl)cyclohexyl]-N-methyl-2-(3,4-dichlorophenyl)acetamide,
trans-N-[2-(1-azetidinyl)cyclohexyl]-N-methyl-2-(3,4-dichlorophenyl)acetamide, and the like, in their (S,S) absolute stereo configuration,
or a pharmacologically acceptable salt thereof.

Compounds of the above Formula I are described and procedures for making them are disclosed in U.S. Pat. Nos. 4,360,531 and 4,359,476 and in U.S. patent application Ser. No. 06/320,635 filed Nov. 12, 1981.

Compounds of the above Formula II are described and procedures for making them are disclosed in U.S. Pat. No. 4,212,878.

Compounds of the above Formula III are described and procedures for making them are disclosed in U.S. Pat. No. 4,145,435.

Compounds of the above Formula IV are described and procedures for making them are disclosed in U.S. Pat. No. 4,360,531.

Compounds of the above Formula V are described and procedures for making them are disclosed in U.S. Pat. No. 4,359,476.

Of these various compounds, a lead compound being selected for advanced studies of the 'water diuretic' property (as well as its analgesic activity) is (5$\alpha$, 7$\alpha$, 8$\beta$)-($\pm$)-3,4-dichloro-N-methyl-N-[7-(1-pyrrolidinyl)-

1-oxaspiro[4.5]dec-8-yl]benzeneacetamide which, as can be seen from the name, is a mixed dextro (+) and levo (−) isomer form of the compound. We now know, however, that for the 'water diuretic' property alone (without considering the analgesic property) the levo (−) isomer of this compound, namely (5α, 7α, 8β)-(−)-3,4-dichloro-N-methyl-N-[7-(1-pyrrolidinyl)-1-oxaspiro[4.5]dec-8-yl]benzeneacetamide is the more potent compound, as illustrated by the rat urinary volume test data below.

The "water diuretic" property of the above Formula I to V compounds was determined by way of the following standard laboratory animal tests.

Studies were conducted in Upjohn/SD (Sprague-Dawley) male rats weighing approximately 160 g. The animals were kept without food overnight and without water one hour before use in these tests. The test compound drugs were given subcutaneously (except where noted) in 1 ml of Vehicle 122 (an aqueous solution of 0.25% methylcellulose). Control animals received the Vehicle 122 only. Each rat received an oral load of 4 ml of carboxymethylcellulose (0.5 percent w/v) in 0.9 percent saline solution (isotonic). The animals were placed in metabolism cages (2 rats/cage) and thereafter spontaneously voided urine was collected for the ensuing five hours. Urine volumes were recorded and in some instances aliquots were saved for analysis. In those instances, urinary electrolytes were quantitated using a Technicon ® 4-channel autoanalyzer.

To illustrate the operation of the above test procedure applied to compounds found to have the 'water diuretic' property pertinent to the invention claimed here, the following detailed examples are provided, without intending that these Examples be limiting upon the scope of the invention.

EXAMPLE 1

Comparison of Urinary Volume and Electrolyte Excretion in Rats Treated With trans-3,4-dichloro-N-methyl-N-[7-(1-pyrrolidinyl)-1,4-dioxaspiro[4.5]dec-8-yl]benzeneacetamide (A) with that of the Control Vehicle Only By the above-described procedure, the above named Structure I compound (A) was administered to rats at per oral (PO) dosages of 0.3, 1.0, 3.0, 10.0, 30.0 and 100 mg/kg of rat body weight. In the Table which follows, T/C is the ratio of the particular parameter (volume, Na+, K+, or Cl−) measured in the treated animals (T) to that parameter measured in the control animals(C).

TABLE 1

Urinary Volume and Electrolyte Excretion Profile in Rats Treated with trans-3,4-dichloro-N-methyl-N-[7-(1-pyrrolidinyl)-1,4-dioxaspiro[4.5]dec-8-yl]benzeneacetamide Administered With An Equal Weight Amount, in Milligrams, of Citric Acid to Assist Dissolution of the Compound (A)

| PO Dose (mg/kg) in Rats | Volume T/C | Na+ T/C | K+ T/C | Cl− T/C |
|---|---|---|---|---|
| 0.3 | 1.0 | 0.8 | 0.8 | 0.9 |
| 1.0 | 1.0 | 1.0 | 0.8 | 1.0 |
| 3.0 | 1.1 | 0.8 | 0.8 | 0.9 |
| 10.0 | 2.2* | 1.2 | 1.3* | 1.1 |
| 30.0 | 3.1* | 1.5* | 1.7* | 1.4* |
| 100.0 | 3.4* | 0.8* | 0.6* | 0.6* |

$T/C = \frac{\text{Parameter measured in treated animals}}{\text{Parameter measured in control animals}}$
*Significant difference from T/C = 1.0

EXAMPLE 2

Comparison of Subcutaneous and Oral Administration Route on Urinary Volume Excretion Rate by trans-3,4-dichloro-N-methyl-N-[7-(1-pyrrolidinyl)-1,4-dioxospiro[4.5]dec-8-yl]-benzeneacetamide (A)

The compound (A) was administered to rats in the above described test, either subcutaneously or orally, at the dosages indicated in the Table below to determine whether or not there was any difference in effect on the rate of urine excretion by the two routes of administration. The results were as follows:

TABLE 2

| Effect of Compound A on Urinary Volume When Given Subcutaneously or Orally to Rats | | |
|---|---|---|
| Dose (mg/kg) In Rats | Urine Volume (T/C) SC | PO |
| 0.1 | 1.9 | — |
| 0.3 | 2.4 | 1.0 |
| 1.0 | 2.9 | 1.0 |
| 3.0 | 3.3 | 1.1 |
| 10.0 | 3.3 | 2.2 |
| 30.0 | 3.0 | 3.1 |
| 100.0 | — | 3.4 |

$T/C = \frac{\text{Urine volume in treated animals}}{\text{Urine volume in control animals}}$
Values are not subjected to statistical analysis.

EXAMPLE 3

T/C Urinary Volume Comparison Ratios For a Number of Additional Compounds Within Formulas I, II, III, IV, and V Above The following additional compounds (with Roman numerals to indicate the appropriate general chemical Structures I, II, III, IV, and V which they exemplify) were tested in the above described rat diuretic test.

| Compound No. | Name and Structure |
|---|---|
| 1 | 3,4-dichloro-N—[[8-(1-pyrrolidinyl)-1,4-dioxaspiro[4.5]dec-8-yl]methyl]benzeneacetamide (II) |
| 2 | trans-3,4-dichloro-N—methyl-N—[8-(1-pyrrolidinyl)-1,4-dioxaspiro[4.5]-dec-7-yl]benzeneacetamide (I) |
| 3 | trans-3,4-dichloro-N—methyl-N—[7-(1-pyrrolidinyl)-1,4-dioxaspiro[4.5]-dec-8-yl]benzeneacetamide (I) |
| 4 | trans-(±)-3,4-dichloro-N—methyl-N—N—[7-(1-pyrrolidinyl)-1,4-dioxaspiro-[4.5]dec-6-yl]benzeneacetamide (I) |
| 5 | trans-4-bromo-N—methyl-N—[7-(1-pyrrolidinyl)-1,4-dioxaspiro[4.5]dec-8-yl]benzamide (I) |
| 6 | (5α,7α,8β)-(±)-3,4-dichloro-N—methyl-N—[7-(1-pyrrolidinyl)-1-oxaspiro[4.5]dec-8-yl]benzeneacetamide (I) |
| 7 | (5α,7α,8β)-(−)-3,4-dichloro-N—methyl-N—[7-(1-pyrrolidinyl)-1-oxaspiro-[4.5]-dec-8-yl]benzeneacetamide (I) |
| 8 | (5ξ,6α,7β)-3,4-dichloro-N—[7-(dimethylamino)-1-oxaspiro[4.5]dec-6-yl]-N—methylbenzeneacetamide (I) |
| 9 | trans-3,4-dichloro-N—methyl-N—[2-(1-pyrrolidinyl)cyclohexyl]benzeneacetamide (U.S. Pat. No. 4,145,435) (III) |
| 10 | trans-N—[2-(allyl(methyl)amino)cyclohexyl]-2-(p-bromophenyl)-N—methylacetamide (III) (U.S. Pat. No. 4,145,435) |
| 11 | trans-2-(p-bromophenyl)-N—[2-(dimethylamino)cyclohexyl]-N—methylacetamide (III) |

TABLE 3

| Compound No. | Name and Structure (U.S. Pat. No. 4,145,435) |
|---|---|

-continued

Urine Volume in Treated Animals(T)/Urine Volume in Control Animals(C)

| Compound | Dosages (SC, mg/kg, in Rats) (T/C Values) | | | | | |
|---|---|---|---|---|---|---|
| | 0.1 | 0.3 | 1.0 | 3.0 | 10.0 | 30.0 |
| 1 | — | — | — | [4.0] | — | — |
| 2 | 0.7 | 0.9 | 1.0 | 1.5 | [2.7] | [3.5] |
| 3 | [1.9] | [2.4] | [2.9] | [3.3] | [3.4] | [3.0] |
| 4 | 1.0 | 1.5 | [2.2] | [2.8] | [2.8] | [3.9] |
| 5 | 0.8 | 1.2 | [1.8] | [2.3] | [2.9] | — |
| 6 | 1.4 | [1.7] | [1.9] | [2.4] | [2.6] | — |
| 7 | 1.6 | [2.1] | [2.7] | [3.1] | [3.4] | [2.4] |
| 8 | 0.6 | 1.2 | [1.7] | [2.6] | [2.7] | [3.3] |
| 9 | 1.1 | 1.3 | [1.8] | [2.7] | [2.8] | [3.2] |
| 10 | 0.6 | 0.5 | 1.0 | 0.5 | 1.2 | [1.6] |
| 11 | 0.8 | 0.9 | 0.7 | 1.4 | [2.4] | [2.3] |

[1] Values shown in boxes are significantly different from T/C = 1.0

The significantly different values for the compounds of Formula I, II, III, IV, and V above are believed to be unique or surprising because other somewhat related compounds and structures did not show significantly different T/C ratios in the same test. The compounds shown to have no significantly different T/C volume excretion ratios relative to untreated control animals were as follows:

| A | trans-3,4-dichloro-N—[2-(dimethylamino)cyclohexyl]-N—methylbenzamide (U.S. Pat. No. 4,098,904) |
|---|---|
| B | cis-3,4-dichloro-N—methyl-N—[2-(1-pyrrolidinyl)cyclohexyl]benzeneacetamide (U.S. Pat. No. 4,098,904) |
| C | trans-3,4-dichloro-N—ethyl-N—[2-(1-pyrrolidinyl)cyclohexyl]benzeneacetamide (U.S. Pat. No. 4,098,904) |
| D | trans-3,4-dichloro-N—methyl-N—[2-(1-piperidinyl)cyclohexyl]benzeneacetamide |
| E | trans-3,4-dichloro-N—methyl-N—[6-(1-pyrrolidinyl)-1,4-dioxaspiro[4.5]dec-7-yl]benzeneacetamide |
| F | trans(±)-3,4-dichloro-N—[7-(dimethylamino)-1,4 dioxaspiro[4.5]dec-8-yl]-N—methylbenzeneacetamide |
| G | (5α,7α,8β)-(+)-3,4-dichloro-N—methyl-N—[7-(1-pyrrolidinyl)-1-oxaspiro[4.5]dec-8-yl]benzeneacetamide |

In additional studies, one of the compounds, compound 3 of Example 3 above, was given to dogs. The dogs were fasted overnight and urine was collected via bladder catheterization from immediately after dosing until 7 hours post dosing. The animals did not have access to water during the study. Urine output in dogs given 10, 30 or 100 μg/kg subcutaneously was 2 to 3.5 times greater than in time-matched control animals. As in rats, enhanced urine output in dogs was not accompanied by significant, consistent increases in urinary electrolyte excretion, i.e., in the dog as in the rat, this agent was a water-only diuretic.

EXAMPLE 4

T/C Urinary Volume Comparison Ratio for trans-(1)-2-(3,4-dichlorophenyl)-N-methyl-N-[2-(1-pyrrolidinyl)cyclohexyl]acetamide maleate The preparation of the titled (Formula III) compound is described in Example 35 in U.S. Pat. No. 4,145,435. This compound has an (S,S) configuration.

In a standard animal diuretic test to determine its T/C (volume) ratio, relative to the untreated control, the above compound had a urinary volume T/C ratio of 3.32, when administered at 40 mg of test compound/kg of animal body weight.

In a similar test with the maleate salt of the trans-(d)-isomer of the maleate salt of the same compound, but having the (R,R) absolute configuration the compound was considered inactive as a water only diuretic, in the same test.

We claim:

1. A process for treating a warm-blooded animal patient suffering from inappropriate hyperhydration which comprises administering to such patient a safe, non-toxic amount sufficient to obtain a water diuretic effect of a compound of the formula selected from the group consisting of

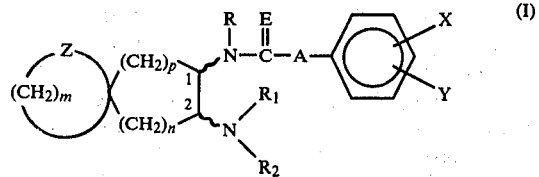

(I)

wherein p is a whole number integer 0, 1 or 2 and n is a whole number integer 1, 2, or 3, so that the resulting cycloaliphatic ring containing them has six (6) carbon atoms;

m is 2 or 3;

A is —$(CH_2)_q$— where q is a whole number integer 1 to 4, —$CH(CH_3)$—; or A is a single chemical bond (—) only when $R_1$ and $R_2$ are taken together with the nitrogen to which they are bonded to complete a ring amine group set forth below;

X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxyacylamino (—NHC(=O)$R_4$ where $R_4$ is hydrogen or $C_1$ to $C_2$-alkyl);

R is hydrogen or $C_1$ to $C_3$-alkyl;

R₁ and R₂, taken separately, are each hydrogen, $C_1$ to $C_3$-alkyl or allyl,

R₁ and R₂, taken together with the nitrogen to which they are bonded, complete a ring selected from the group consisting of azetidinyl, pyrrolidinyl and piperidinyl, pyrrolyl, 3-pyrrolinyl, 3-azabicyclo[3.1.0]-hexan-3-yl and 3-azabicyclo[3.2.0]heptan-3-yl;

E is oxygen or sulfur;

Z is selected from the group consisting of oxygen, bivalent sulfur, and sulfinyl;

provided that the diuretically active formula I compound contains an isomer thereof with an S absolute structural configuration at each of the 1- and 2-positions of the cyclohexane ring carbons bonded to the nitrogen atoms, or a pharmacologically acceptable salt thereof.

2. A process according to claim 1 wherein the active diuretic compound is one of Formula I in which p is 2;

n is 1;

m is 2;

X and Y are a halogen having an atomic number of from 9 to 35;

R is $C_1$ to $C_3$-alkyl;

R₁ and R₂ are taken together with the nitrogen to which they are bonded to complete a pyrrolidinyl ring;

E is oxygen;

A is —CH₂;

Z is oxygen (—O—);

or a pharmaceutically acceptable salt thereof.

3. A process according to claim 2 wherein the active diuretic compound is (5α,7α,8β)-(±)-3,4-dichloro-N-methyl-N[7-(1-pyrrolidinyl)-1-oxaspiro[4.5]dec-8-yl]benzeneacetamide, or a pharmaceutically acceptable salt thereof.

4. A process according to claim 2 wherein the active diuretic compound is (5α,7α,8β)-(−)-3,4-dichloro-N-methyl-N-[7-(1-pyrrolidinyl)-1-oxaspiro[4.5]dec-8-yl]benzeneacetamide, or a pharmaceutically acceptable salt thereof.

* * * * *

UNITED STATES PATENT AND TRADEMARK OFFICE
CERTIFICATE OF CORRECTION

PATENT NO. : 4,463,013

DATED : July 31, 1984

INVENTOR(S) : Robert J. Collins et al.

It is certified that error appears in the above-identified patent and that said Letters Patent is hereby corrected as shown below:

Abstract, part of formula IV and V should read as follows:

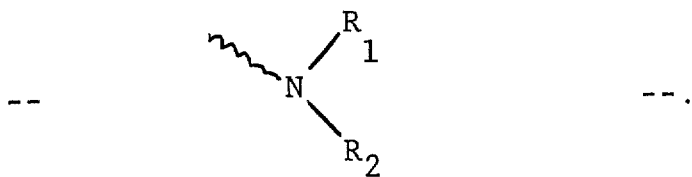

Column 14, claim 3, line 14, "N[7-(1-pyrrolidinyl)" should read -- N-[7-(1-pyrrolidinyl) --.

Signed and Sealed this

Fifteenth Day of April 1986

[SEAL]

Attest:

DONALD J. QUIGG

Attesting Officer

Commissioner of Patents and Trademarks